United States Patent [19]

Olin

[11] 3,996,275
[45] Dec. 7, 1976

[54] DITHIOCARBAMATE HYDROCHLORIDE SALTS AND THEIR MANUFACTURE

[75] Inventor: John F. Olin, Ballwin, Mo.

[73] Assignee: Monsanto Company, St. Louis, Mo.

[22] Filed: Jan. 21, 1976

[21] Appl. No.: 651,096

Related U.S. Application Data

[62] Division of Ser. No. 567,050, April 10, 1975, Pat. No. 3,956,384, which is a division of Ser. No. 506,671, Sept. 16, 1974, Pat. No. 3,903,153, which is a division of Ser. No. 382,259, July 24, 1973, Pat. No. 3,860,634, which is a division of Ser. No. 160,556, July 7, 1971, abandoned.

[52] U.S. Cl. .......................................... 260/545 R
[51] Int. Cl.² ...................................... C07C 153/00
[58] Field of Search .................... 260/545 R, 455 A

[56] References Cited

UNITED STATES PATENTS 3,138,628   6/1964   Sijpesteijn .................... 260/455 A

*Primary Examiner*—Gerald A. Schwartz
*Attorney, Agent, or Firm*—Richard H. Shear

[57] ABSTRACT

N,N-disubstituted-N'-arylamidino dialkyldithiocarbamate hydrochlorides are prepared by reaction of trisubstituted thioureas with disubstituted thiocarbamoyl chlorides. N,N-disubstituted-N'-arylamidino dialkyldithiocarbamate hydrochlorides are particularly useful as pre-emergent and contact herbicides.

6 Claims, No Drawings

DITHIOCARBAMATE HYDROCHLORIDE SALTS AND THEIR MANUFACTURE

This is a division of application Ser. No. 567,050 filed Apr. 10, 1975, now U.S. Pat. No. 3,956,384, which is a division of Ser. No. 506,671, now U.S. Pat. No. 3,903,153, which is a division of Ser. No. 382,259, now U.S. Pat. No. 3,860,634 which in turn is a division of Ser. No. 160,556, now abandoned.

This invention relates to novel dithiocarbamate hydrochloride salts of the formula

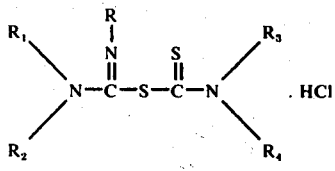

which dithiocarbamate hydrochloride salts of this invention may be readily prepared by reacting a trisubstituted thiourea of the formula

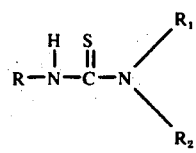

with a disubstituted thiocarbamoyl chloride of the formula

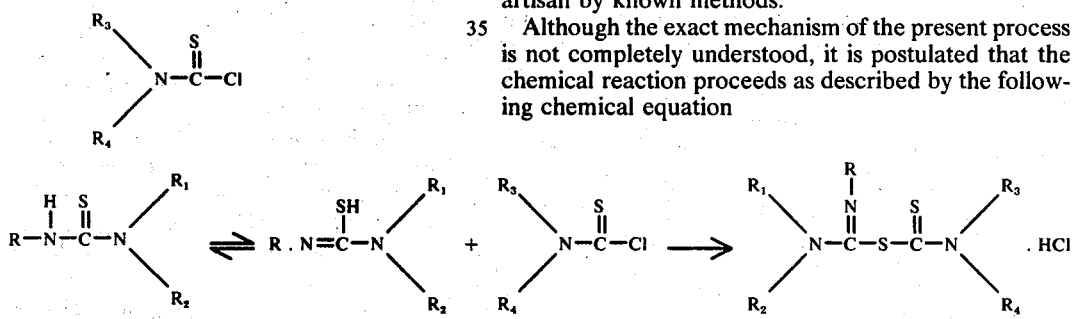

wherein R is naphthyl or

wherein $n$ is an integer of from 0 to 3 and X is halo, trihalomethyl, hydroxyl, lower alkyl, lower alkoxy, lower alkoxyalkyl, lower acylamido, lower alkacyl, lower alkylcarbamoyloxy or acyloxy of the formula $C_mH_{2m+1}COO-$ wherein $m$ is an integer of from 1 to 8, $R_1$ and $R_2$ are each lower alkyl, lower alkenyl, lower alkynyl or benzyl having from 0 to 2 halo on the phenyl ring, and $R_3$ and $R_4$ are each lower alkyl or benzyl having from 0 to 1 halo on the phenyl ring.

Lower alkyl is alkyl having from 1 to 5 carbons. Examples of lower alkyl include, but are not limited to, methyl, ethyl, propyl, isopropyl, butyl, sec-butyl, isobutyl, tert-butyl, and pentyl. Preferred lower alkyl are ethyl and methyl.

Lower alkoxy have from 1 to 5 carbons. Examples of alkoxy include, but are not limited to, methoxy, ethoxy, propoxy, butoxy, pentoxy and their isomers. Lower alkoxyalkyl have from 2 to 8 carbons, for example, propoxymethyl, butoxybutyl, butoxyethyl, methoxymethyl and ethoxypropyl.

Halo is a halogen selected from the group consisting of fluorine, chlorine, bromine and iodine. Preferred halo is chloro.

Lower alkenyl and lower alkynyl have from 2 through 5 carbons. Examples of lower alkenyl include, but are not limited to, allyl and crotyl. Examples of lower alkynyl include, but are not limited to, 2-propynyl (propargyl), 2-butynyl, and 3-butynyl.

Lower alkacyl are represented by the expression, lower alkyl-CO-. Lower acylamido are represented by the expression, lower alkyl—CO—NH—. Lower alkylcarbamoyloxy are represented by the expression, lower alkyl-NH—COO—.

Products of this invention are useful as biocides. Exemplary of such biocidal uses for these products is the control of nematodes, arachnids, arthropods, molluscs and insects as well as eradication of noxious weeds. Compounds of this invention are particularly useful as pre-emergent and contact herbicides.

Substituted thioureas and disubstituted thiocarbamoyl chlorides useful in the process of the present invention for the preparation of the novel compounds described herein are known compounds which are commercially available or may be prepared by the skilled artisan by known methods.

Although the exact mechanism of the present process is not completely understood, it is postulated that the chemical reaction proceeds as described by the following chemical equation

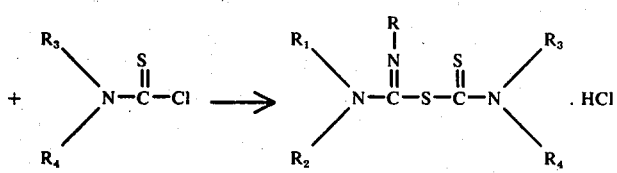

The reaction may be carried out at a temperature from about room temperature (approximately 20° Centigrade) to about 150° Centigrade (°C.), but preferably from about 35° C. to about 100° C.

High yields and rapid reaction rates are obtained when the reaction is conducted under reflux conditions. When conducting the reaction at reflux the presence of an inert solvent is not necessary. Close control of reaction conditions, particularly the amount of heat added to the reaction system, will allow conduct of the reaction at elevated temperatures without the presence of an inert solvent in a suitable open or closed vessel. It is advantageous, particularly in a commercial process, to conduct the reaction in a less strictly controlled environment. Therefore, it is preferred to conduct the reaction at reflux in the presence of an inert solvent, and more preferred to conduct the reaction in the presence of an inert organic liquid which is a solvent for the reactants but not a solvent for the N,N-disubstituted-N'-arylamidino dialkyldithiocarbamate hydrochloride products of the reaction. The boiling of the inert solvent or inert organic liquid under reflux provides facile control of the reaction mass temperature.

Although conducting the reaction under reflux is preferred, the reaction may also be carried out in an open or closed vessel. Similarly, the reaction is generally conducted at atmospheric pressure but higher or lower pressures may be used since pressure is not a critical variable in the successful conduct of the process. To promote the homogeneity of the reaction mass, it is preferred to agitate the reaction mass during the course of the reaction, although agitation is not a necessary part of the present process.

Although the described trisubstituted thiourea and disubstituted thiocarbamoyl chloride will react regardless of the proportional amounts in which the two reactants are present, it is preferred that the molecular proportion of said disubstituted thiocarbamoyl chloride be approximately equal to the molecular proportion of said trisubstituted thiourea. It is more preferred that said disubstituted thiocarbamoyl chloride be present at least in an equimolecular amount as compared to said trisubstituted thiourea, and still more preferred that said disubstituted thiocarbamoyl chloride be present in slight excess of an equimolecular amount.

The reaction mass may consist only of the aforedescribed reactants and their reaction products or it may contain other components in addition such diluents, other inert materials and solvents, i.e., common organic liquids which are inert under the reaction conditions and which may dissolve one or more of the reactants or products of the reaction, which solvents are exemplified by but not limited to ketones such as acetone, methyl ethyl ketone, methyl isobutyl ketone, etc., aliphatic hydrocarbons such as pentane, hexane, mineral spirits, etc., aromatics such as benzene, toluene, xylenes, etc., ethers such as diethyl ether, diisopropyl ether, etc., esters such as methyl acetate, ethyl acetate, propyl acetate, etc., and other organics such as tetrahydrofurane, etc. Preferred solvents are inert organic liquids which dissolve the reactants but not the desired reaction products which are products of this invention. Examples of preferred solvents are ketones, ethers and esters. More preferred solvents are ketones, ethers and esters with boiling points from about 35° C. to about 100° C. Preferably, the reaction is conducted under anhydrous conditions although small quantities of water may be present, up to about 2 percent by weight of the total reaction mass. The presence of water does not prevent the reaction from occurring but causes hydrolysis of the disubstituted thiocarbamoyl chloride which, in turn, decreases the yield of the desired products and results in contamination of the reaction mass with

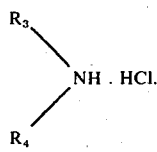

As illustrative of this invention but not limitative thereof is the following:

EXAMPLE 1

To a suitable reaction vessel equipped with an agitator, thermometer and reflux condenser are charged approximately 18 grams (g.), about 0.1 mole, of 1,1-dimethyl-3-phenyl-2-thiourea, approximately 12.4 g. (about 0.1 mole) of dimethylthiocarbamoyl chloride and about 100 milliliters (ml.) of reagent grade acetone. The so-charged vessel is heated to raise the temperature of the stirred reaction mass to its boiling point. The particles of said thiourea dissolve giving a light straw-colored solution. Upon commencement of boiling of the solution, a solid precipitate appears. The mass is maintained at reflux for about 10 minutes. Thereupon an additional volume of acetone is added to the mass, the mass is slurried and the precipitate is separated from the liquid by filtration. After washing twice with 50 ml. volumes of acetone the white powder having a melting point of about 126 to 127° C. is air dried and identified as N,N-dimethyl-N'-phenylamidino dimethyldithiocarbamate hydrochloride,

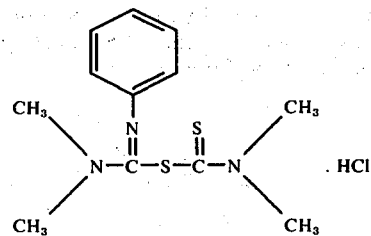

Calculated for $C_{12}H_{17}N_3S_2.HCl$: C, 47.4; H, 6.0; Cl, 11.7; N, 13.8; S, 27.1. Found: C, 47.6; H, 6.2; Cl, 11.9; N, 13.9; S, 21.2.

EXAMPLE 2

To a suitable reaction vessel equipped with an agitator, thermometer and reflux condenser are charged approximately 18 g. (about 0.1 mole) of 1,1-dimethyl-3-phenyl-2-thiourea, approximately 12.4 g. (about 0.1 mole) of diethylthiocarbamoyl chloride and about 100 ml. of reagent grade acetone. The so-charged vessel is heated to raise the temperature of the stirred reaction mass to its boiling point. The particles of said thiourea dissolve giving a light straw-colored solution. Upon commencement of boiling of the solution, a solid precipitate appears. The mass is maintained at reflux for about 10 minutes. Thereupon an additional volume of acetone is added to the mass, the mass is slurried and the precipitate is separated from the liquid by filtration. After washing twice with 50 ml. volumes of acetone the white powder with a melting point of about 129 to 130° C. is air dried and identified as N,N-dimethyl-N'-phenylamidino diethyldithiocarbamate hydrochloride,

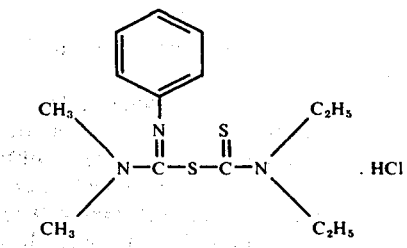

Calculated for $C_{14}H_{21}N_3S_2.HCl$: C, 50.7; H, 6.7; S, 19.3. Found: C, 50.9; H, 6.8; S, 19.5.

EXAMPLES 3 through 7

Utilizing the procedure of Example 2 but substituting for 1,1-dimethyl-3-phenyl-2-thiourea an equimolecular proportion of the trisubstituted thiourea of Column A and substituting for diethylthiocarbamoyl chloride and equimolecular proportion of the disubstituted thiocarbamoyl chloride of Column B the dithiocarbamate hydrochloride salt of Column C is obtained.

| Example | A | B | C |
|---|---|---|---|
| 3 | 1,1-dipentyl-3-phenyl-2-thiourea | dipentylthio-carbamoyl chloride | N,N-dipentyl-N'-phenylamidino dipentyldithio-carbamate hydrochloride |
| 4 | 1,1-diisopropyl-3-phenyl-2-thiourea | dibenzylthio-carbamoyl chloride | N,N-diisopropyl-N'-phenylamidino dibenzyldithio-carbamate hydrochloride |
| 5 | 1,1-disecbutyl-3-phenyl-2-thiourea | ethylmethylthio-carbamoyl chloride | N,N-disecbutyl-N'-phenylamidino ethylmethyl-dithiocarbamate hydrochloride |
| 6 | 1-ethyl-1-methyl-3-phenyl-2-thiourea | di-(chloromethyl)-thiocarbamoyl chloride | N-ethyl, N-methyl-N'-phenylamidino di-(chloromethyl)-dithiocarbamate hydrochloride |
| 7 | 1,1-dipropyl-3-naphthyl-2-thiourea | isobutylmethyl thiocarbamoyl chloride | N,N-dipropyl-N'-naphthylamidino isobutylmethyl-dithiocarbamate hydrochloride |

EXAMPLE 8

To a suitable reaction vessel equipped with a thermometer, agitator and reflux condenser are charged approximately 62.3 g. (about 0.25 mole) of 1-(3,4-dichlorophenyl)-3,3-dimethylthiourea and 200 g. of chloroform. To the so-charged stirred mass is added approximately 33 g. of dimethylthiocarbamoyl chloride dissolved in 50 g. of chloroform over a period of 5 minutes. The reaction mass is slowly warmed to boiling, giving a clear solution at about 50° C. The mass is gently refluxed for about ½ hour, cooled and evaporated using a rotary evaporator. The solid residue which is a white powder with a melting point of about 159 to 162° C. remaining is identified as N'-(3,4-dichlorophenyl)-N,N-dimethylamidino dimethyldithiocarbamate hydrochloride,

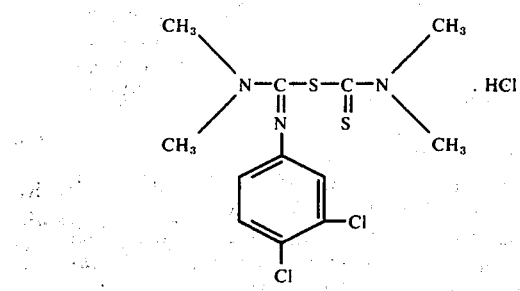

Calculated for $C_{12}H_{15}Cl_2N_3S_2 \cdot HCl$: C, 38.7; H, 4.3; S, 17.2. Found: C, 38.6; H, 4.3; S, 17.1.

EXAMPLE 9

To a suitable reaction vessel are charged approximately 18 g. (about 0.072 mole) of 1-(3,4-dichlorophenyl)-3,3-dimethyl-2-thiourea, about 125 ml. of acetone and approximately 15.2 g. (about 0.1 mole) of diethylthiocarbamoyl chloride. The vessel is warmed sufficiently to give a clear solution of its contents and thereafter is allowed to cool to room temperature, about 20° C., and to remain at about that temperature for about 9 days. Thereafter, a crystalline product is separated from the reaction mass, washed twice with approximately 50 ml. volumes of acetone, determined to be a colorless solid with a melting point of about 123° to 124° C., and identified as N'-(3,4-dichlorophenyl)-N,N-dimethylamidino diethyldithiocarbamate hydrochloride

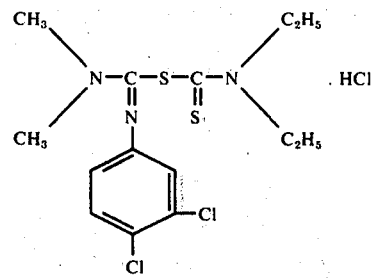

Calculated for $C_{14}H_{19}Cl_2N_3S_2 \cdot HCl$: C, 42.0; H, 5.0; S, 16.0. Found: C, 42.1; H, 5.2; S, 15.9.

EXAMPLES 10 through 23

Utilizing the procedure of Example 2 but substituting for 1,1-dimethyl-3-phenyl-2-thiourea an equimolecular proportion of the trisubstituted thiourea of Column A the dithiocarbamate hydrochloride salt of Column B is obtained

| Example | A | B |
|---|---|---|
| 10 | 1-(3,4,5-trichlorophenyl)-3,3-diisopropyl-2-thiourea | N'-(3,4,5-trichlorohenyl)-N,N-diisopropylamidino |

-continued

| Example | A | B |
|---|---|---|
| 11 | 1-(2,6-difluorophenyl)-3,3-dibutyl-2-thiourea | N'-(2,6-difluorophenyl)-N,N-dibutylamidino diethyldithiocarbamate hydrochloride |
| 12 | 1-(para-bromophenyl)-3-ethyl-3-propyl-2-thiourea | N'-(para-bromophenyl)-N-ethyl-N-propylamidino diethyldithiocarbamate hydrochloride |
| 13 | 1-benzyl-1-tert-butyl-3-(ortho-chlorophenyl)-2-thiourea | N-benzyl-N-tert-butyl-N'-(ortho-chlorophenyl)-amidino diethyldithiocarbamate hydrochloride |
| 14 | 1,1-dimethyl-3-(alpha,alpha,alpha,trifluorometatolyl)-2-thiourea | N,N-dimethyl-N'-(alpha,alpha,alpha-trifluorometatolyl)-amidino diethyldithiocarbamate hydrochloride |
| 15 | 1,1-diethyl-3-(ortho-tolyl)-2-thiourea | N,N-diethyl-N'-(ortho-tolyl)-amidino diethyldithiocarbamate hydrochloride |
| 16 | 1,1-diisobutyl-3-(meta-cumenyl)-3-thiourea | N,N-diisobutyl-N'-(meta-cumenyl)-amidino diethyldithiocarbamate hydrochloride |
| 17 | 1,1-dipentyl-3-(para-xylyl)-2-thiourea | N,N-dipentyl-N'-(para-xylyl)-amidino diethyldithiocarbamate hydrochloride |
| 18 | 1,1-dimethyl-3-(ortho-methoxyphenyl)-2-thiourea | N,N-dimethyl-N'-(ortho-methoxyphenyl)-amidino diethyldithiocarbamate hydrochloride |
| 19 | 1,1-diethyl-3-(para-ethoxyphenyl)-2-thiourea | N,N-diethyl-N'-(para-ethoxyphenyl)-amidino diethyldithiocarbamate hydrochloride |
| 20 | 1,1-diallyl-3-(3,4-dichlorophenyl)-2-thiourea | N,N-diallyl-N'-(3,4-dichlorophenyl) amidino diethyldithiocarbamate hydrochloride |
| 21 | 1-(para-chlorophenyl)-3-methyl-3-propargyl-2-thiourea | N'-(para-chlorophenyl)-N-methyl-N-propargylamidino diethyldithiocarbamate hydrochloride |
| 22 | 1,1-di-(2-chloroallyl)-3-(3,4-dichlorophenyl-2-thiourea | N,N-di-(2-chloroallyl)-N'-(3,4-dichlorophenyl)-amidino diethyldithiocarbamate hydrochloride |
| 23 | 1,1-di-(2,3-dichloroallyl)-3-(3,4-dichlorophenyl)-2-thiourea | N,N-di-(2,3-dichloroallyl)-N'-(3,4-dichlorophenyl)-amidino diethyldithiocarbamate hydrochloride |

EXAMPLE 24

To a suitable reaction vessel equipped with a thermometer, agitator and reflux condenser are charged approximately 19.6 g. (about 0.1 mole) of 1-(meta-hydroxyphenyl)-3,3-dimethyl-2-thiourea, approximately 15 g. of dimethylthiocarbamoyl chloride and about 100 ml. of dry acetone. The vessel is heated to raise the temperature of the stirred contents to reflux. When the temperature reaches about 50° C. a clear solution is obtained but as the temperature continues to rise clouding appears and a sandy precipitate forms. After refluxing for about 1 hour, the vessel is allowed to cool to room temperature. The solid material is separated from the liquid component by filtration, washed twice with about 35 ml. volumes of acetone, air-dried, determined to be a cream-colored solid which decomposes above about 135° C., and identified as N,N-dimethyl-N'-(meta-hydroxyphenyl)-amidino dimethyldithiocarbamate hydrochloride

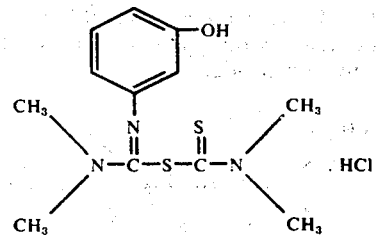

Calculated for $C_{12}H_{17}N_3OS_2 \cdot HCl$: C, 45.1; H, 5.7; Cl, 11.1. Found: C, 45.2; H, 5.7; Cl, 11.0.

In similar fashion other N,N-disubstituted-N'-(hydroxyaryl)-amidino dialkyldithiocarbamate hydrochlorides such as N,N-diethyl-N'-(ortho-hydroxyphenyl)-amidino dimethyldithiocarbamate hydrochloride, N-ethyl-N-methyl-N'-(para-hydroxyphenyl)-amidino dimethyldithiocarbamate hydrochloride, N,N-diethyl-N'-(3,4-dihydroxyphenyl)-amidino diethyldithiocarbamate hydrochloride, N,N-dimethyl-N'-(2,6-dihydroxyphenyl)-amidino diethyldithiocarbamate hydrochloride and the like may be prepared.

EXAMPLE 25

To a suitable reaction vessel equipped with a thermometer and reflux condenser are charged approximately 11.1 g. (about 0.05 mole) of 1-(para-acetylphenyl)-3,3-dimethyl-2-thiourea, about 100 ml of acetone and approximately 7.4 g. (0.06 mole) of dimethylthiocarbamoyl chloride. The vessel is heated to bring the contents to reflux temperature and the contents are refluxed for about ½ hour. Upon cooling to room temperature a light tan precipitate appears which is separated from the liquid by filtration, found to have an irregular melting point of about 120° to 125° C., and identified as N'-(para-acetylphenyl)-N,N-dimethylamidino dimethyldithiocarbamate hydrochloride

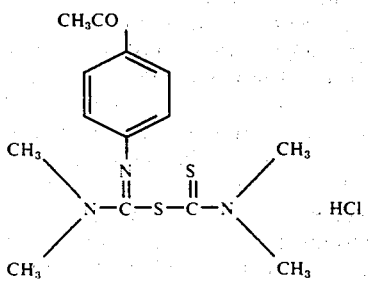

Calculated for $C_{14}H_{19}N_3OS_2 \cdot HCl$: C, 48.6; H, 5.8; S, 18.5. Found: C, 48.5; H, 6.0; S, 18.4.

In a similar manner other N,N-disubstituted-N'-(acylphenyl)-amidino dialkyldithiocarbamate hydrochlorides such as N'-(meta-acetylphenyl)-N,N-diethylamidino diethyldithiocarbamate hydrochloride, N'-(ortho-acetylphenyl)-N,N-dimethylamidino diethyldithiocarbamate hydrochloride, N'-(meta-propionylphenyl)-N,N-dimethylamidino dimethyldithiocarbamate hydrochloride. N'-(para-butyrylphenyl)-N,N-diethylamidino diethyldithiocarbamate hydrochloride and the like may be prepared.

EXAMPLE 26

To a suitable reaction vessel equipped with a thermometer, agitator and reflux condenser are charged approximately 28 g. (about 0.1 mole) of 1,1-dimethyl-3-(meta-pivalamidophenyl)-2-thiourea, about 100 ml. of dry acetone and approximately 15 grams (about 0.12 mole) of dimethyl carbamoyl chloride. The vessel is heated to bring the contents to reflux and the contents are refluxed with stirring for about ½ hour. Thereafter to the clear, straw-colored solution is added about 75 ml. of hexane. Upon cooling to about room temperature, approximately 20° C., the solution turns to a creamy white slurry. The precipitate is separated from the liquid by slow filtration, washed alternately with small quantities of acetone and hexane, air-dried, determined to be an off-white solid which decomposes at about 131° C., and identified as N,N-dimethyl-N'-(meta-pivalamidophenyl)-amidino dimethyldithiocarbamate hydrochloride

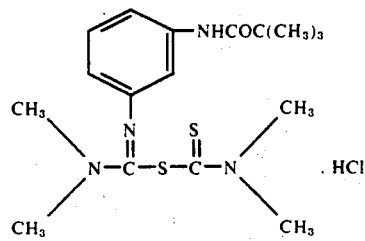

Calculated for $C_{17}H_{26}N_4OS_2 \cdot HCl$: C, 50.7; H, 6.8; Cl, 8.8; S, 15.9. Found: C, 50.6; H, 6.9; Cl, 8.7; S, 15.8.

Similarly, other N,N-disubstituted-N'-(acylamidoaryl)-amidino dialkyldithiocarbamate hydrochlorides such as N'-(para-acetamidophenyl)-N,N-diethylamidino diethyldithiocarbamate hydrochloride, N,N-dimethyl-N'-(meta-propionamidophenyl)-amidino dimethyl-dithiocarbamate hydrochloride and the like may be prepared.

EXAMPLE 27

To a suitable reaction vessel are charged approximately 14 g. (about 0.05 mole) of butyl para-(dimethylthiocarbamido) benzoate dissolved in about 100 ml. of dry acetone and approximately 7.4 g. (about 0.05 mole) of dimethylcarbamoyl chloride. The contents are maintained at about room temperature (approximately 20° C.) for about 3 days. A copious precipitate forms which is separated from the remainder of the contents of the vessel, washed twice with 25 ml. volumes of acetone, air-dried, determined to be an off-white solid with an irregular melting point of about 129° to 133°40 C. and identified as butyl-para-[(dimethylamino)mercaptomethylene]amino benzoate, dimethyldithiocarbamate hydrochloride

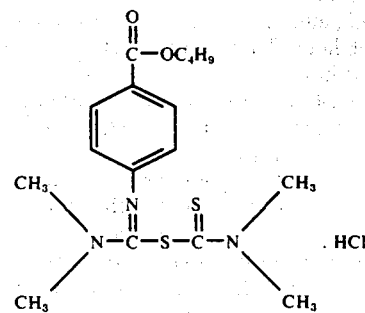

Calculated for $C_{17}H_{25}N_3O_2S_2 \cdot HCl$: C, 50.5; H, 6.5; S, 15.9. Found: C, 50.6; H, 6.6; S, 15.8.

EXAMPLE 28

To a suitable reaction vessel are charged approximately 16.8 g. (about 0.05 mole) of octyl para-(dimethylthiocarbamido)-benzoate dissolved in about 100 ml. of dry-acetone and approximately 7.4 g. (about 0.05 mole) of dimethylcarbamoyl chloride. The contents are maintained at about room temperature (approximately 20° C) for about 3 days. A copious white precipitate forms which is separated from the remainder of the contents of the vessel, washed twice with 25 ml. volumes of acetone, air-dried, determined to be a white solid with an irregular melting point of about 128° to 131° C., and identified as octyl para-[(dimethylamino)mercaptomethylene]amino benzoate, dimethyldithiocarbamate hydrochloride

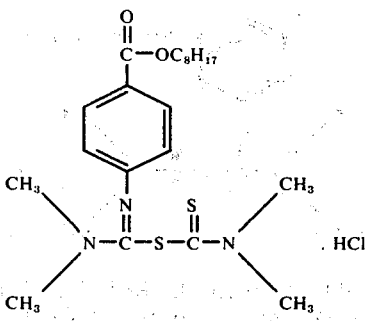

Calculated for $C_{21}H_{33}N_3O_2S \cdot HCl$: C, 54.8; H, 7.5; S, 13.7. Found: C, 54.9; H, 7.7; S, 13.9.

EXAMPLE 29

1,1-(meta-methylcarbamoyloxyphenyl)-3-(meta-merthylcarbamoyloxyphenyl)-2-thiourea is prepared by charging to a suitable equipped reaction vessel about 32.7 parts by weight of 1,1-dimethyl-3-(meta-hydroxyphenyl)-2-thiourea, about 100 parts by weight of ethyl acetate, about 12 parts by weight of methyl isocyanate and about 1 part by weight triethylamine, refluxing for about 1 hour with stirring, diluting the resulting slurry with about 100 parts by weight of hexane, cooling to about 20° C., recovering the precipitate from the remainder by filtration, washing the recovered solid with ethyl acetate and hexane and air drying.

To a suitable reaction vessel equipped with reflux condenser, agitator and thermometer is charged approximately 12.65 g. (about 0.05 mole) of 1,1-dimethyl-3-(meta-methylcarbamoyloxyphenyl)-2-thiourea, approximately 10 g. of dimethylthiocarbamoyl chloride and about 100 ml. of reagent grade acetone. The vessel is heated to bring the contents to reflux temperature, about 60° C., and the contents are refluxed with stirring for about ½ hour. Thereafter about 75 ml. of hexane is added to the hot mass. The mass is then cooled to about 15° C. and filtered to recover precipitated material from the remainder of the contents. The recovered solid is washed with a mixture of 2 parts by volume acetone and 1 part by volume hexane, air-dried, determined to be a colorless solid with a melting point of about 124 to 127° C., and identified as meta-[(dimethylamino) mercaptomethylene]aminophenyl methylcarbamate, dimethyldithiocarbamate hydrochloride

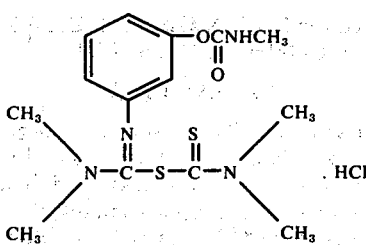

Calculated for $C_{14}H_{20}N_4O_2S_2 \cdot HCl$: C, 44.6; H, 5.6; Cl, 9.4; N, 14.9. Found: C, 44.7; H, 5.6; Cl, 9.4; N, 15.0.

EXAMPLE 30

1-(meta-hydroxyphenyl)-3,3-dimethyl-2-thiourea, tert-butylcarbamate is prepared by charging to a suitable vessel about 25 g. (approximately 0.1 mole) meta-hydroxyphenyl isothiocyanate, tert-butylcarbamate dissolved in about 150 ml. of methanol, and adding, with stirring about 15.4 g. (approximately 0.12 moles) of 40 percent aqueous dimethylamine mixed with about 50 ml. of methanol in a single increment. The mass quickly solidifies as the temperature rises from about room temperature to about 60° C. The mass is cooled to about 15° C., separated from the residual liquid by filtration, washed with four 150 ml. portions of a 75 percent methanol/25 percent water solution and dried under vacuum overnight.

To a suitable reaction vessel equipped with reflux condenser, agitator and thermometer is charged approximately 25 g. (about 0.084 mole) of 1-(meta-hydroxyphenyl)-3,3-dimethyl-2-thiourea, tert-butyl carbamate, approximately 13.9 g. of diethylthiocarbamoyl chloride (about 0.092 mole) and about 250 ml. of reagent grade acetone. The vessel is heated with stirring to bring the contents to reflux temperature, about 60° C., and the contents are refluxed with stirring for about 2½ hours. Although the slurry thins, solution is not achieved. The mass is then cooled overnight to about room temperature (approximately 20° C.) and filtered to recoveer precipitated material from the remainder of the contents. The recovered solid is washed withh two 100 ml. portions of a mixture of 1 part by volume acetone and 1 part by volume hexane, air-dried, determined to be a fluffy white powder with a melting point of about 132° C., and identified as meta-[(dimethylamino)mercaptomethylene]aminophenyl, tert-butyl carbamate, diethyl-dithiocarbamate hydrochloride

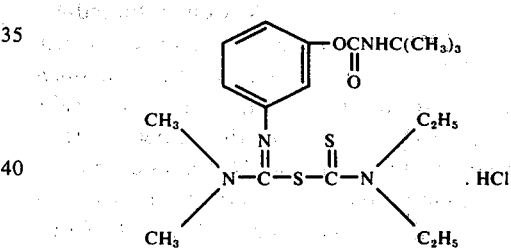

Calculated for $C_{19}H_{30}N_4O_2S_2 \cdot HCl$: C, 51.0; H, 7.0; N, 12.5; S, 14.3. Found: C, 51.1; H, 7.0; N, 12.6; S, 14.2. In similar manner other N,N-disubstituted-N'-lower alkylcarbamoyloxyphenyl dialkyldithiocarbamate hydrochlorides may likewise be prepared.

EXAMPLE 31

This example illustrates that the present method of preparation is not suitable for reactions based upon disubstituted carbamoyl (oxygen) chlorides of the formula

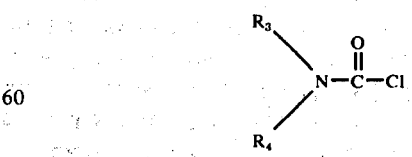

wherein $R_3$ and $R_4$ are each alkyl or substituted alkyl.

To a suitable reaction vessel are charged about 10.5 g. (approximately 0.042 mole) of 1-(3,4-dichlorophenyl)-3,3-dimethyl-2-thiourea, about 65 ml. of anhydrous acetone and about 8.6 g. (approximately 0.08 mole) of dimethylcarbamoyl chloride. The vessel is warmed to about 40° C. to produce solution of its contents. The vessel is cooled to room temperature (about 20° C.) and a massive crop of crystals appear. The crystals are separated from the remainder of the contents by filtration and identified as 1-(3,4-dichlorophenyl)-3,3-dimethyl-2-thiourea. It is concluded no reaction takes place.

The above procedure is repeated except that, in place of dimethylcarbamoyl chloride, about 9.4 g. (approximately 0.07 mole) of diethylcarbamoyl chloride is charged to the vessel. Again starting thiourea is recovered and it is concluded that no reaction takes place.

EXAMPLE 32

In greenhouse tests, seeds of 16 different plants, each representing a principal botanical type, were planted in 9-inch by 13-inch by 2-inch aluminum pans which were level filled with the prepared soil. The soil was compacted to approximately ⅜ inch below the top, 5 corn planted down the center with 5 soybeans on one side and 5 cotton on the other. The grass species plus pigweed were scattered over ⅓ of the pan, broadleaf species were scattered on the next ⅓ and both barnyard grass and rice were planted in the remaining ⅓ of the pan. A measured amount of barnyard grass and rice was planted in rows (10–20 seeds each). The seeds were covered with untreated soil and grown for contact use.

After the plants were 21 days old, each aluminum pan was sprayed with a solution of the candidate chemical. Each herbicidal solution was prepared from an appropriate quantity of a 2 percent solution of the candidate compound in dimethyl formamide diluted with acetone, 0.4 ml. of a 3:1 cyclohexanone emulsifying agent mixture, and water to give a volume of 15 ml. of an emulsion of the concentration of the candidate compound shown in Table I. The emulsifying agent was a mixture comprising 35 wt. percent butylamine dodecylbenzene sulfonate and 65 wt. percent of a tall oil-ethylene oxide condensate having about 6 moles of ethylene oxide per mole of tall oil.

The watering of the seeds was accomplished by placing the aluminum pans in a sand bench having ½ inch depth of water thereon and permitting the soil in the pans to absorb moisture through the perforated bottom of the pans.

The planted pans were thereafter placed on a wet sand bench in a greenhouse and maintained there for 14 days under ordinary conditions of sunlight and watering. At the end of this time, the plants were observed and the results recorded. The herbicidal rating was obtained by means of a fixed scale based on the average percent germination of each seed lot. The herbicidal ratings are defined as follows:

| 0 | No phytotoxicity. |
|---|---|
| 1 | Slight phytotoxocity. |
| 2 | Moderate phytotoxicity. |
| 3 | Severe phytotoxicity. |
| 4 | Plants all dead |
| — | Not tested. |

Individual injury ratings for each plant type are reported in Table I.

Herbicidal solution concentrations of 0.2 percent, 0.05 percent, and 0.01 percent are substantially equivalent to application rates of 4 pounds per acre, 1 pound per acre, and 0.2 pound per acre, respectively.

TABLE I

| Compound Example No. | N'-(3,4-dichlorophenyl)-N,N-dimethylamidino dimethyldithiocarbamate hydrochloride 8 | | | N'-(3,4-dichlorophenyl)-N,N-dimethylamidino diethyldithiocarbamate hydrochloride 9 | | |
|---|---|---|---|---|---|---|
| Herbicidal Solution Concentration (Percent) | 0.2 | 0.05 | 0.01 | 0.2 | 0.05 | 0.01 |
| Cotton | 2 | 1 | 1 | 2 | 0 | 0 |
| Corn | 3 | 3 | 1 | 4 | 3 | 1 |
| Soybean | 4 | 4 | 0 | 4 | 4 | 0 |
| Cocklebur | 4 | — | — | 4 | 4 | 0 |
| Crab Grass | 4 | 3 | 2 | 4 | 3 | 1 |
| Lambsquarter | 4 | 4 | 4 | 4 | 4 | 4 |
| Wild Oat | 3 | 2 | 0 | 1 | 3 | 0 |
| Smartweed | 4 | 4 | 0 | 4 | 3 | 0 |
| Brome | 3 | 3 | 1 | 3 | 3 | 2 |
| Pigweed | 4 | 4 | 3 | 4 | 4 | 3 |
| Barnyard Grass | 3 | 3 | 2 | 3 | 2 | 1 |
| Sugar Beet | 4 | 4 | 1 | 4 | 4 | 0 |
| Wheat | 3 | 3 | 1 | 2 | 2 | 0 |
| Velvet Leaf | 4 | 3 | 0 | 4 | 3 | 0 |
| Rice | 4 | 3 | 2 | 3 | 2 | 1 |
| Coffee Weed | 4 | 3 | 1 | 4 | 2 | 0 |

EXAMPLE 33

Contact herbicidal activity of representative N,N-disubstituted-N'-arylamidino dialkylthiocarbamate hydrochlorides of this invention is determined by the following procedure: The compound to be tested is applied in spray form to plants of a given age of several grasses and broadleaf plants. After the plants are the desired age, each aluminum pan is sprayed with a given volume of a 0.5 percent concentration solution of the candidate chemical, corresponding to a rate of approximately 10 lbs. per acre. This solution is prepared from an aliquot of a 2 percent solution of the candidate compound in acetone, a known amount of cyclohexanone-emulsifying agent mix, and sufficient water to make up to volume. The emulsifying agent is a mixture comprising 35 wt. percent butylamine dodecylbenzene sulfonate and 65 wt. percent of a tall oil-ethylene oxide condensate having about 6 moles of ethylene oxide per mole of tall oil. The injuries to the plants are then observed approximately 14 days later and the results are recorded.

Contact herbicidal activity of the compounds prepared in the designated Examples is observed against the species as shown in Table II. X denotes that herbicidal activity is observed.

TABLE II

| Compound of Example No. | 1 | 2 | 8 | 9 | 26 | 27 | 29 |
|---|---|---|---|---|---|---|---|
| Species |   |   |   |   |   |   |   |
| Morning Glory | X | X | X | X | X | X | X |
| Wild Oat | X | X | X | X |   |   | X |
| Rye Grass | X |   | X | X |   |   |   |
| Radish | X | X | X | X | X | X | X |
| Sugar Beets | X | X | X | X | X | X | X |
| Foxtail | X | X | X | X | X |   | X |
| Crabgrass | X | X | X | X | X |   | X |
| Pigweed | X | X | X | X | X | X | X |
| Soybean | X | X | X | X | X |   | X |
| Wild Buckwheat | X | X | X | X | X | X | X |
| Tomato | X | X | X | X | X |   | X |
| Sorghum | X | X | X | X |   |   | X |
| Brome Grass |   |   | X | X |   |   | X |

EXAMPLE 34

Pre-emergent herbicidal activity of representative N,N-disubstituted-N'-arylamidino dialkyldithiocarbamate hydrochlorides of this invention is determined by the following procedure. A good grade of top soil is placed in aluminum pans and compacted to a depth of ⅜ to ½ inch from the top of the pan. A pre-determined number of seeds of each of several plant species are placed on top of the soil in the pans. The seeds are covered with soil and the pans leveled. The herbicidal composition is applied by spraying the surface of the top layer of soil with a solution containing a sufficient amount of active ingredient to obtain a rate of application of 5 lbs. per acre. The pans are then placed on a sand bench in the greenhouse and watered from below as needed. The plants are observed at the end of approximately 14 days and the results recorded.

Pre-emergent activity of the compounds prepared in the designated Examples is observed against the species as shown in Table III. X denotes that herbicidal activity is observed.

TABLE III

| Compound of Example No. | 1 | 2 | 8 | 9 |
|---|---|---|---|---|
| Species |   |   |   |   |
| Wild Oat | X |   |   |   |
| Morning Glory | X | X |   |   |
| Radish | X | X | X |   |
| Sugar Beets | X |   | X |   |
| Foxtail | X | X | X | X |
| Crabgrass | X | X | X | X |
| Pigweed | X | X | X |   |
| Wild Buckwheat | X |   | X | X |
| Tomato | X |   | X |   |
| Sorghum | X | X |   |   |
| Soybean |   | X |   |   |
| Brome Grass |   |   |   |   |

The compounds of the present invention can be employed in a method of inhibiting the growth of unwanted vegetation which comprises applying to the area to be protected a herbicidally effective amount of the compound. Such a method may utilize application of the compound to the soil or directly to the foliage of the vegetation.

In using the compounds of the present invention as pre-emergent and contact herbicides, the compounds can be used alone or in combination with a material referred to in the art as an adjuvant in liquid or solid form. Herbicidal formulations are prepared by admixing the compound which is the active ingredient of the formulation with an adjuvant including diluents, extenders, carriers and conditioning agents to provide compositions in the form of finely-divided particulate solids, granules, pellets, solutions, dispersions or emulsions. Thus, the compounds of this invention are preferably used with an adjuvent such as a liqud of organic origin and, if mixed within about an hour before application, water, a wetting agent, dispersing agent, an emulsifying agent or any suitable combination of these. The herbicidal formulations usually contain from about 0.01 percent to about 99 percent by weight of the active ingredient. Application of these formulations to the soil or growth media can be carried out by simply admixing with the soil, by applying to the surface of the soil and thereafter dragging or discing into the soil to the desired depth, or by employing a liquid carrier to accomplish the penetration and impregnation. The application of herbicidal formulations to the surface of soil or to above ground portions of plants can be carried out by conventional methods, e.g. power, boom and hand sprayers. The formulations can also be applied from airplanes as a spray because of their effectiveness at low dosages. In a further method, the distribution of the active ingredients in soil can be carried out by admixture with the water employed to irrigate the soil. In such procedures, the amount of water can be varied with the porosity and water holding capacity of the soil to obtain the desired depth of distribution of the active ingredients.

The exact amount of active ingredient to be employed is dependent upon the response desired in the plant as well as such other factors as the plant species and stage of development thereof, the specific soil and depth at which the active ingredients are distributed in the soil and the amount of rainfall as well as the specific active ingredient employed. In foliar treatment, the active ingredients are applied in amounts from about 1 to about 50 or more pounds per acre. In applications to soil for the control of the growth of germinant seeds, germinative seeds, emerging seedlings and established vegetation, the active ingredients are applied in amounts from about 0.1 to about 25 or more pounds per acre. It is believed that one skilled in the art can readily determine from the teachings of this specification the general procedure for any application.

While this invention has been described with respect to certain embodiments it is to be understood that it is not so limited and that variations and modifications thereof obvious to those skilled in the art to which this invention appertains can be made without departing from the spirit or scope thereof.

What is claimed is:

1. A compound of the formula

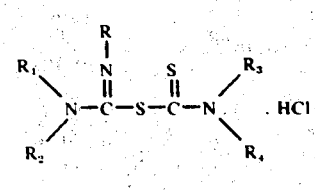

wherein R is

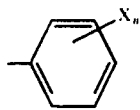

wherein *n* is an integer of from 1 to 3 and X is lower alkyl-CO-NH-, $R_1$ and $R_2$ are each lower alkyl, lower alkenyl, lower alkynyl or benzyl having from 0 to 2 halo on the phenyl ring, and $R_3$ and $R_4$ are each lower alkyl or benzyl having from 0 to 1 halo on the phenyl ring.

2. A compound of claim 1 wherein $R_1$, $R_2$, $R_3$ and $R_4$ are each lower alkyl.

3. A compound of claim 2 wherein the lower alkyl is methyl or ethyl.

4. A compound of claim 1 wherein $R_1$, $R_2$, $R_3$, and $R_4$ are each lower alkyl.

5. A compound of claim 4 wherein the lower alkyl is methyl or ethyl and *n* is an integer of from 1 to 3.

6. The compound of claim 1 which is N,N-dimethyl-N'-(meta-pivalamido-phenyl)-amidino dimethyldithiocarbamate hydrochloride.

* * * * *